United States Patent [19] [11] 3,934,586
Easton et al. [45] Jan. 27, 1976

[54] NON-REFILLABLE MULTIPLE DOSAGE SYRINGE
[76] Inventors: Fred H. Easton, 11591 Capri Drive, Garden Grove, Calif. 92641; N. Donald Helmer, 10-63rd Place, Long Beach, Calif. 90803
[22] Filed: Jan. 22, 1975
[21] Appl. No.: 543,030

[52] U.S. Cl. ............... 128/235; 128/218 C; 222/47
[51] Int. Cl.² ........................................... A61M 1/00
[58] Field of Search ........... 128/235, 234, 224, 218, 128/213, 214, 215, 216; 222/23, 43, 47

[56] References Cited
UNITED STATES PATENTS
| 2,474,496 | 6/1949 | Rayman | 128/218 C |
| 2,764,981 | 10/1956 | Helmer et al. | 128/218 C |
| 2,844,148 | 7/1958 | Raife | 128/218 C |
| 2,869,541 | 1/1959 | Helmer et al. | 128/218 C |

FOREIGN PATENTS OR APPLICATIONS
6,908,371   6/1969   Netherlands .................. 128/218 C Primary Examiner—Robert W. Michell
Assistant Examiner—J. Yasko
Attorney, Agent, or Firm—Donald D. Mon

[57] ABSTRACT

A multiple dosage syringe comprises a hollow barrel through which a piston slides by being pushed by a piston member protruding from the rear of the barrel so that liquid material within the barrel is discharged through a discharge member at the front end of the barrel. A plurality of longitudinally spaced stops protrude outwardly from the perimeter of the piston member which protrudes from the rear of the barrel so that the foremost stop abuts a flange at the rear of the barrel. To discharge a dosage this stop is broken off along a line of maximum weakness so that the stop can enter the barrel during the discharge of the dosage which is completed when the next stop strikes the flange. This process is repeated for each dosage. The line of maximum weakness extends obliquely from the junction of the forward end of the stop with the exterior of the piston member and is spaced somewhat away from the outer surface of the piston member at the rear, so that the outer part of the stop will break off along this line of weakness. The rear part of the stop is undercut inside the line of breaking off so that there is left a sharp edge which acts to score the inner surface of the barrel during progress through the barrel so that the barrel is not re-useable for another filling of liquid material.

5 Claims, 5 Drawing Figures

U.S. Patent    Jan. 27, 1976    3,934,586
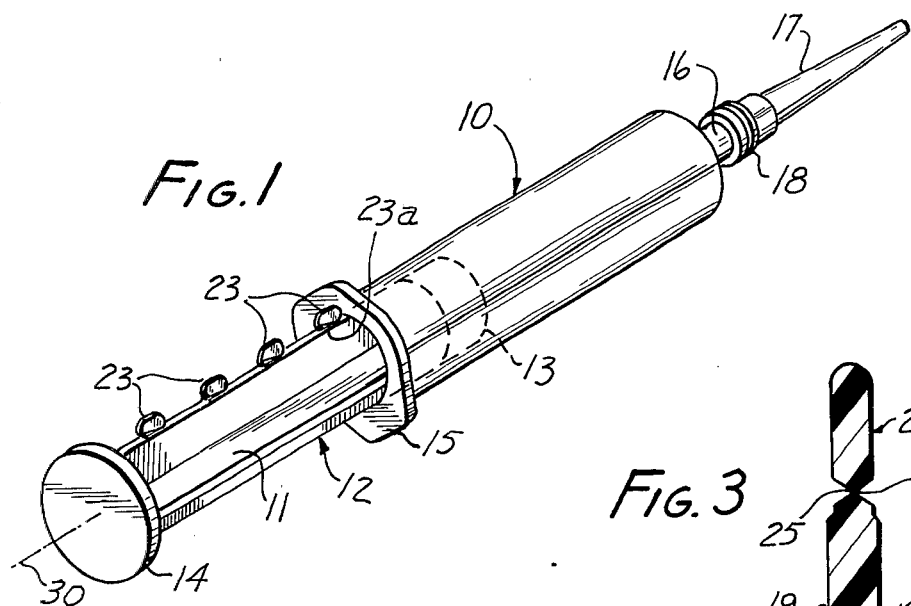
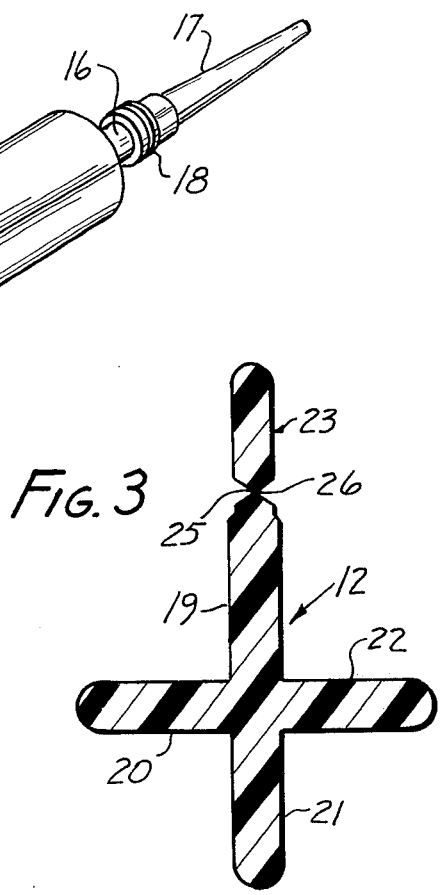
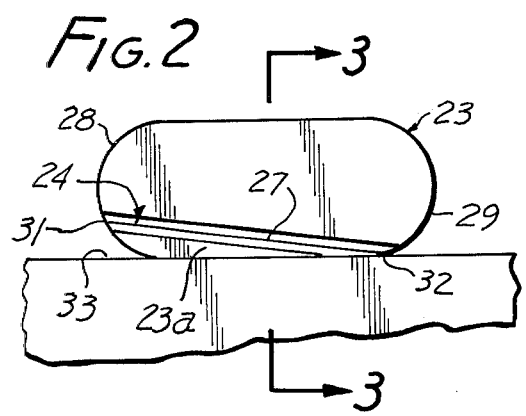
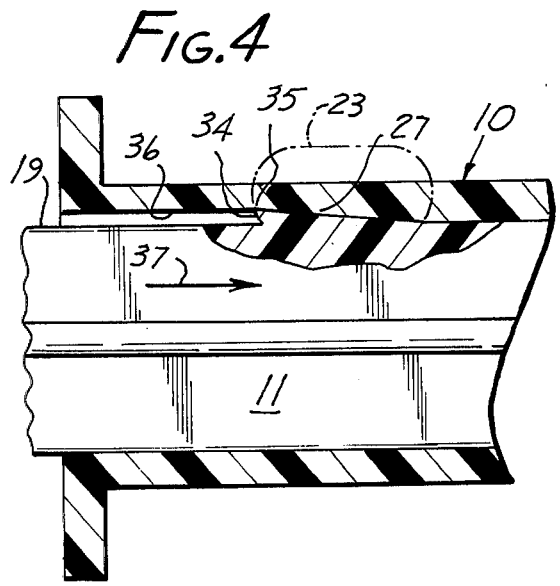
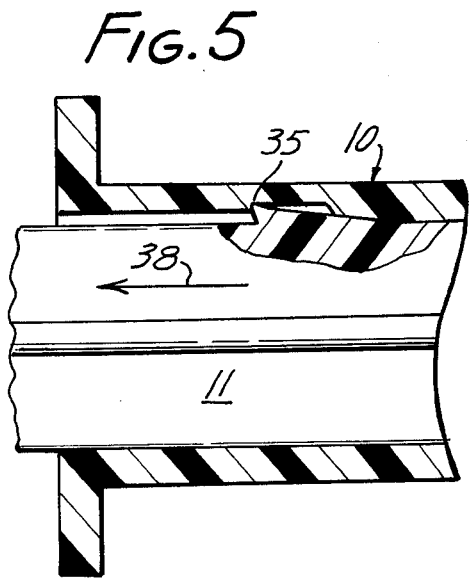

NON-REFILLABLE MULTIPLE DOSAGE SYRINGE

The present invention relates generally to the field of dispensing devices, and more particularly to an improved multiple dosage syringe that automatically indicates when each of a number of doses of predetermined volume has been dispensed therefrom.

This invention is an improvement on that shown and claimed in U.S. Pat. No. 2,764,981 issued Oct. 2, 1956. In that patent there is illustrated and described a multi-dosage disposable syringe particularly useful in the dairy industry for treating cows infected by mastitis by the injection of fluid material into the teats for combating the infection. The syringes of that patent include provision for injecting a plurality of equal measured doses, ordinarily four doses which would provide treatment for one cow.

More specifically, that patent discloses an elongate barrel capable of holding a plurality of doses of the liquid material; a discharge device at one end of the barrel through which each of the doses is discharged; a piston slidably mounted in the barrel and attached to an elongate piston member extending rearwardly from the piston through the end of the barrel opposite that of the discharge device and a plurality of longitudinally spaced stops attached to the elongate member to restrict further movement of the piston through the barrel toward the discharge device after discharge of a measured dose of the liquid. In one embodiment shown in that patent the stops are made brittle enough so that they may be broken off to allow further progress of the piston through the barrel for injecting another dose.

A disadvantage of the syringes shown in that patent is that the syringes are inherently refillable after their original doses have been discharged. Refilling of syringes is undesirable. One reason why refilling is undesirable resides in the fact that a used syringe according to that patent has its stops removed or broken off so that the dosages cannot again be accurately measured. A second reason for the undesirability of refilling resides in the fact that in most such instances of refilling, the consumer or refiller does not ordinarily have the facility for excluding contamination such as bacterial contamination or the like. Good practice requires that the syringe from which the dosage is delivered shall be disposed of after use.

It is an object of the present invention to provide means rendering a syringe un-usable after its dosage has been completely discharged.

The invention is carried out by providing longitudinally spaced stops somewhat similar to those shown in said U.S. Pat. No. 2,764,981 but provided with an undercut providing a line of greatest weakness of the stop which extends rearwardly relative to the discharge device and outwardly from the elongate piston member. Thus the stop can be broken off along the said line of greatest weakness leaving only a relatively small extent of the stop material protruding so that the plunger stop can still be pushed forwardly through the barrel and allowing the stop member also to pass through the barrel. The rear edge of the stop, however, will score the wall of the barrel especially when the piston is withdrawn rearwardly from the discharge end. Such scoring is sufficient to prevent the drawing into the barrel of a refilling of the liquid material after the initial liquid dosage material is discharged.

A preferred feature especially effective during a rearward movement of the piston resides in undercutting each stop from the rearmost end of the said line of greatest weakness. This will provide an even sharper edge or point at the rear end of the remaining part of the stop, which will have even greater effectiveness in scoring the barrel.

The foregoing and other features of the invention will be better understood from the following detailed description and the accompanying drawing of which:

FIG. 1 is an isometric view of a syringe provided with an improvement according to this invention;

FIG. 2 is an enlaged elevation view showing a detail of the mounting of one of the stops on the elongate piston member;

FIG. 3 is a cross-section view taken at line 3—3 of FIG. 1;

FIG. 4 is an enlarged cross-section view showing part of the barrel and part of the elongate piston member within the barrel after the major portion of a stop has been broken off and showing the scoring of the barrel during a forward stroke; and FIG. 5 is a view similar to FIG. 4 but illustrating the further scoring of the barrel during the rearward stroke of the piston.

Referring to the drawing there is shown in FIG. 1 an elongated hollow barrel 10 in which a plunger 11 is slidably mounted through the rear end of the barrel. The forward end of the barrel is narrowed down to a neck 16 to which a hollow tubular discharge device 17 having a small discharge opening is attached by threads so that when the barrel 10 is filled with liquid material a forward sliding of the plunger causes the liquid to be discharged through the discharge device 17. The plunger 11 comprises an elongate piston member 12 having attached to its forward end a piston 13 shown in phantom in FIG. 1 and a disc-shaped head 14 attached to its rear end so that when the piston is moved forwardly through the barrel to a position at or close to the forward end of the barrel the head 14 will strike a flange 15 attached to the rear end of the barrel to stop further forward movement.

Piston member 12 is a rigid elongate member having a cross-section in the general form of a cross formed by four legs 19, 20, 21 and 22 which extend outwardly from the central axis of the elongate member, the two legs 19 and 21 being collinear and perpendicular to the two legs 20 and 22 which are also collinear. The disc 14 at the rear of member 12 is attached to the four legs.

The barrel 10 is preferably molded as a one piece unit from a suitable synthetic resin of which a number are well known and readily available for the purpose. The discharge device 17 including its nut 18 is also preferably molded of a similar synthetic resin and likewise the piston member 12 with its disc 14 are preferably molded in one piece of a similar synthetic resin. The piston 13 is also preferably an integral part of the plunger 11 but will commonly be provided with a circumferential resilient O-ring set at the circumference of a groove formed in the piston in a well-known manner to act as a seal for the liquid within the barrel.

Leg 19 has a number of longitudinally spaced protuberances 23 integral with the leg 19 and protruding outwardly from its periphery. Each protuberance 23 is joined to the outer edge of leg 19 by a section 24 of reduced thickness relative to the thickness of the leg and of the protuberance, formed by undercuts 25 and 26 at opposite sides of the leg and protuberance providing a straight line 27 of minimum thickness and maximum weakness. The rear end 28 and forward end 29 of the protuberance 23 are rounded as is best seen in FIG. 3. The undercut area 24 is oblique relative to the central axis 30 of the syringe (this axis 30 being colinear with the central axis of the elongate member) and to the outer edge of leg 19 such that the line 27 of maximum weakness is a straight line whose rearward end 31 is a distance outside the outer edge 33 of leg 19 and the forward end 32 of the line meets the outer edge of the leg where the curved end 29 meets the leg.

Because of the relative weakness at the line 27 the protuberance 23 can readily be broken away from the leg by exerting a lateral push against the protuberance, which will leave attached to the leg that part of the protuberance lying inside the line 27 as can be seen in FIG. 4 wherein the part of the protuberance 23 which had been outside the line 27 is indicated in phantom. Because of the curvature 28 at the rear end of the protuberance there is an undercut 34 at the rear end of what remains of the protuberance after the breaking away of its upper part, which leaves a relatively sharp pointed edge 35 pointing rearwardly. The term "undercut" as used herein dos not necessarily signify an actual cutting operation, but rather signifies the shape given to the component part under discussion during is manufacture which may be by molding.

When the barrel 10 of the multiple dosage syringe is filled with fluid material, the piston member 11 is in a rearward position with its protuberances 23 situated outside the confines of the barrel as shown in FIG. 1. To apply the first dose of fluid contained in the syringe the forwardmost protuberance 23, which has been acting as a stop against forward movement of the piston, is now broken off, as described above, along the line 27. Since the remaining portion 23a of the protuberance does not extend greatly beyond the outer edge 33 of the leg 19 it can enter the barrel 10 as shown in FIG. 4 because there is enough tolerance between the extremities of the four legs of piston member 11 to permit this. Furthermore, the material of portion 23a is sufficiently hard so that it scores the inner wall of the barrel longitudinally along a score line 36 as the piston member is pushed forwardly by pressure from the operator on the outer surface of disc 14 in the direction of arrow 37 shown in FIG. 4.

The operator will push the piston forwardly through the barrel unitl the next protuberance or stop 23 abuts the flange 15. The operator will feel this stopping of the piston which will signify to him the discharge of one dosage. To discharge the second dosage the operator will go through the same procedure as in the case of the first dosage by first breaking off the outer part of the second protuberance and then pushing forwardly until the third stop reaches the flange 15 which will signify completion of the discharge of the second dosage. This operation will be continued stop by stop until all the dosages in the syringe are discharged, which in the case illustrated will be four dosages for the treatment of one cow.

Upon the discharge of all the dosages, the syringe should be discarded and a new syringe loaded with fluid material should be used for the next cow. If, however, it were attempted to re-use the same syringe, after discharge of all its dosages, for a re-filling with another quantity of fluid material it would be necesssary to retract the plunger by pulling the piston member rearwardly. This would cause the sharp edge 35 to dig further in the wall of the barrel to deepen the score line or produce a new deep score line as the piston member moves rearwardly in the direction of arrow 38. If after thus scoring the barrel it were attempted to re-use the syringe by re-filling it, the score mark or marks would prevent an adequate seal between the piston 13 and the barrel to operate properly to discharge proper dosages, for the reason that the fluid would leak past the sealing element of the piston, normally an O-ring, through the score line or lines.

It will be understood that the embodiments of the invention illustrated and described herein are given by way of illustration and not of limitation, and that modifications or equivalents or alternatives within the scope of the invention may suggest themselves to those skilled in the art.

I claim:

1. In a multiple dosage syringe that automatically signals to the user's sense of feel when a dose of predetermined volume has been discharged therefrom, including: an elongate hollow barrel capable of holding a charge comprising a plurality of such doses of a liquid material; discharge means mounted on the forward end of said barrel through which each of said doses can be discharged from said barrel; a piston slidably mounted within said barrel; an elongate piston member having a central axis, affixed to said piston and extending rearwardly through the rear end of said barrel; and stop means operatively associated with said barrel and member that tend to restrict forward movement of said piston after a dose of said liquid material is discharged through said discharge means, and stop means comprising a plurality of longitudinally spaced stops formed on the periphery of said elongate piston member, each of said stops having a greater longitudinal dimension than its transverse thickness dimension and each stop protruding outwardly from the periphery of the elongate member to such an extent that it will strike a member at the rear end of said barrel when said piston member is moved forwardly, each of said stops being sufficiently removable from its outwardly projecting position to permit said piston member and piston to move further forward within said barrel toward said discharge member; the improvement comprising:

a longitudinal undercut providing a line of maximum weakness of each stop extending in a longitudinal plane obliquely outward in the rearward direction relative to the central axis of the elongate member so that the portion of the stop outside said line can be broken off, leaving an inner portion of the stop protruding somewhat outside the elongate member, the amount of the protrusion of said inner portion being sufficiently slight so that the protrusion can move through the barrel in the direction, the rear end of the protrusion having an edge which scores the inner wall of the barrel during movement of the piston member sufficiently to prevent a sufficient seal between the piston and the barrel wall to permit discharging accurate quantitative doses from a fresh charge of liquid material after the original charge has been discharged.

2. The improvement according to claim 1 in which the line is a straight line.

3. The improvement according to claim 1 in which the line meets the forward part of the stop at an outer edge of the piston member and is some distance from said outer edge at the rear of the stop.

4. The improvement according to claim 1 in which the protrusion is undercut at the rear of the stop creating a rearwardly directed edge.

5. The improvement according to claim 1 in which the line is formed by an undercut of the protrusion.

* * * * *

UNITED STATES PATENT OFFICE
CERTIFICATE OF CORRECTION

Patent No. 3,934,586                    Dated January 27, 1976

Inventor(s) FRED H. EASTON ET AL

It is certified that error appears in the above-identified patent and that said Letters Patent are hereby corrected as shown below:

| | |
|---|---|
| Col. 2, line 11 | "enlaged" should read --enlarged-- |
| Col. 3, line 24 | "is" should read --its-- |
| Col. 3, line 46 | "unitl" should read --until-- |
| Col. 4, line 28 | "and" should read --said-- |

Signed and Sealed this

Fourth Day of January 1977

[SEAL]

Attest:

RUTH C. MASON
*Attesting Officer*

C. MARSHALL DANN
*Commissioner of Patents and Trademarks*